United States Patent
Hara

(10) Patent No.: US 8,119,824 B2
(45) Date of Patent: Feb. 21, 2012

(54) PROCESSES FOR PRODUCING HIGHER FATTY ACID ESTERS

(75) Inventor: Michikazu Hara, Yokohama (JP)

(73) Assignee: Tokyo Institute of Technology, Tokyo (JP)

( * ) Notice: Subject to any disclaimer, the term of this patent is extended or adjusted under 35 U.S.C. 154(b) by 175 days.

(21) Appl. No.: 11/921,511

(22) PCT Filed: Jun. 20, 2006

(86) PCT No.: PCT/JP2006/312323
§ 371 (c)(1),
(2), (4) Date: Dec. 4, 2007

(87) PCT Pub. No.: WO2007/000913
PCT Pub. Date: Jan. 4, 2007

(65) Prior Publication Data
US 2009/0131709 A1 May 21, 2009

Related U.S. Application Data

(60) Provisional application No. 60/694,070, filed on Jun. 27, 2005.

(51) Int. Cl.
*C07C 51/00* (2006.01)
*C07C 69/58* (2006.01)

(52) U.S. Cl. ........ 554/163; 560/129; 554/169; 554/164; 554/167; 554/170

(58) Field of Classification Search .................. 554/163, 554/164, 167, 170
See application file for complete search history.

(56) References Cited

U.S. PATENT DOCUMENTS 3,584,061 A * 6/1971 Olstowski et al. ............ 568/728
(Continued)

FOREIGN PATENT DOCUMENTS

EP 1 331 260 7/2003
(Continued)

OTHER PUBLICATIONS

Child R., et al., Compositon of Coconut Shells, 1938, Journal of the Ameican Chemical Society, vol. 60, No. 6, 1506-1507.*

(Continued)

*Primary Examiner* — Yate' K. Cutliff
(74) *Attorney, Agent, or Firm* — Birch, Stewart, Kolasch & Birch, LLP

(57) ABSTRACT

As means for producing a biodiesel oil from a feed oil containing a free fatty acid at high efficiency, the following processes (1) to (3) are provided: (1) a process for producing a higher fatty acid ester, comprising reacting a lower alcohol with a higher fatty acid in the presence of an amorphous carbon having a sulfonate group introduced therein, thereby producing the higher fatty acid ester; (2) a process for producing a higher fatty acid ester, comprising reacting a lower alcohol with a higher fatty acid and a higher fatty acid triglyceride in the presence of an amorphous carbon having a sulfonate group introduced therein, thereby producing the higher fatty acid ester by both of the reaction between the lower alcohol and the higher fatty acid and the reaction between the lower alcohol and the higher fatty acid triglyceride; and (3) a process for producing a higher fatty acid ester, comprising: reacting a lower alcohol with a higher fatty acid and a higher fatty acid triglyceride in the presence of an amorphous carbon having a sulfonate group introduced therein, thereby producing the higher fatty acid ester by both of the reaction between the lower alcohol and the higher fatty acid and the reaction between the lower alcohol and the higher fatty acid triglyceride; and reacting the unreacted lower alcohol with the unreacted higher fatty acid triglyceride in the presence of an alkali hydroxide, thereby producing the higher fatty acid ester.

16 Claims, 1 Drawing Sheet

U.S. PATENT DOCUMENTS

| | | | |
|---|---|---|---|
| 4,652,406 A * | 3/1987 | Lepper et al. | 554/167 |
| 2003/0004363 A1 | 1/2003 | Koncar et al. | |
| 2003/0083514 A1 | 5/2003 | Boocock | |

FOREIGN PATENT DOCUMENTS

| | | |
|---|---|---|
| JP | 7-224002 A | 8/1995 |
| JP | 10-139726 A | 5/1998 |
| JP | 2003-507495 A | 2/2003 |
| JP | 2004-510044 A | 4/2004 |
| JP | 2004-238311 A | 8/2004 |
| WO | WO-2005/029508 A1 | 3/2005 |

OTHER PUBLICATIONS

Schuchardt, U., et al. Transesterification of Vegetable Oils; a Review;, 1998, Journal of the Brazilian Chemical Society, vol. 9, No. 1, pp. 199-210.*

Hara, M. et al., Angewandte Chemie, 2004, vol. 43, No. 22, pp. 2955-2958.

Toda, M. et al., Nature, Nov. 10, 2005, vol. 438, pp. 178.

Extended European Search Report issued in European Patent Application No. 06766984.6 on May 7, 2010.

* cited by examiner

PROCESSES FOR PRODUCING HIGHER FATTY ACID ESTERS

This application is the National Phase of PCT/JP2006/312323 filed on Jun. 20, 2006, which claims priority under 35 U.S.C. 119(e) to U.S. Provisional Application No. 60/694,070 filed on Jun. 27, 2005. The entire contents of which are hereby incorporated by reference.

FIELD OF THE INVENTION

The present invention relates to a process for producing a higher fatty acid ester at high efficiency. The higher fatty acid ester produced by the process is useful as a diesel fuel or the like.

BACKGROUND ART

A methyl or ethyl ester of a higher fatty acid (e.g., oleic acid, stearic acid) that is contained in a fruit or seed of a plant in abundance is called a clean diesel fuel "a biodiesel oil" and has been focused as one of the next generation fuels. A biodiesel oil can be used as a fuel for existing diesel engines. A biodiesel oil produces an exhaust gas free of any sulfur component upon being combusted, and the amount of black smoke generated by the combustion is remarkably reduced compared to a conventional diesel fuel that is generated from petroleum. More importantly, $CO_2$ produced by the combustion of a biodiesel oil is fixed again in a plant during the growth stage of the plant; in other words, a biodiesel oil is a zero $CO_2$ emission fuel. If the cultivation, harvest and treatment of a crop containing a higher fatty acid in abundance and the production reaction, separation and purification of a biodiesel oil from the crop can be achieved at good efficiency, a clean energy of higher quality could be produced. For these reasons, an interest in biodiesel oils has been growing year by year, and the amount of biodiesel oils produced in the world is estimated to exceed 1,700,000 kl in 2005. While the amount of production of biodiesel oils in European countries where many diesel vehicles are used accounts for 99% of the total production amount, the amount of production of biodiesel oils in Japan accounts for only about 0.1%.

In European countries, a biodiesel oil is produced in large quantity by using a crude oil produced by expressing a crop such as soybean as a raw material. However, a "free fatty acid" contained in the crude oil becomes a stumbling block for the efficient production of a biodiesel oil. A crude oil contains an oil-and-fat (triglyceride; an ester between a higher fatty acid and glycerin) and a considerable amount of a free fatty acid (which is a higher fatty acid present in a free form, not in the form of an oil-and-fat). What we generally call "edible oil" is one produced by removing a free fatty acid from a crude oil. When an alcohol and an alkali hydroxide are added to an oil-and-fat, a transesterification occurs by the basic catalytic action of the alkali hydroxide to thereby produce a higher fatty acid ester (a biodiesel oil) and glycerin. However, when it is tried to synthesize a biodiesel oil by adding an alcohol and an alkali hydroxide to a plant-derived crude oil, a reaction between a free fatty acid with the alkali occurs preceding to the transesterification and, as a result, a soap and water are produced. Water deteriorates the catalytic action of an alkali remarkably. Further, a product may be contaminated by water produced during the reaction by the action of a soap that can act as a surfactant. Therefore, the presence of water makes the synthesis and separation of a biodiesel oil difficult. For the purpose of producing a biodiesel oil from a plant-derived crude oil in large quantity and at high efficiency, a free fatty acid is usually removed from the crude oil. However, the removal of a free fatty acid requires an enormous amount of energy. In recent years, a process has also been employed in which a free higher fatty acid contained in a crude oil is converted into a biodiesel oil by the esterification using an acid catalyst and the oil-and-fat remaining in the reaction system is then converted into a biodiesel oil in a conventional manner. However, since there is no solid acid catalyst which enables the efficient proceeding of the esterification, the reaction in the first stage of the process has no choice but to rely on a liquid acid such as sulfuric acid and hydrochloric acid. As mentioned above, when a liquid acid is used as a catalyst, an enormous amount of energy is necessary for separating a product from the catalyst after the reaction. Thus, for the production of a biodiesel oil, a large amount of energy is used for the separation and purification of the biodiesel oil, which accounts for 20 to 50% of the cost required for the mass production of a biodiesel oil.

On the other hand, the present inventors have found that an amorphous carbon having a sulfonate group introduced therein can act as a solid catalyst and already filed patent applications (Patent reference Nos. 1 and 2). Although these patent applications describe that the carbon can catalyzes the esterification between ethanol and acetic acid, it is not described that the carbon can catalyze the esterification between ethanol and a higher fatty acid.

[Patent reference No. 1] Japanese Patent Application Laid-open No. 2004-238311
[Patent reference No. 2] International Publication No. WO 2005/029508

DISCLOSURE OF THE INVENTION

Problems to be Solved by the Invention

As mentioned above, the production of a biodiesel oil from a feed oil containing a free fatty acid, such as a plant-derived crude oil, requires a complicated step such as separation and purification. Under these technical situations, the object of the present invention is to provide means for producing a biodiesel oil from a feed oil containing a free fatty acid at high efficiency.

Means for Solving the Problems

In order to solve the problems as mentioned above, the present inventors have made intensive and extensive studies. As a result, it is found that an amorphous carbon having a sulfonate group introduced therein which has been developed by the present inventors previously has an excellent catalytic activity on the esterification between a lower alcohol and a higher fatty acid and the transesterification between a lower alcohol and a higher fatty acid triglyceride.

As mentioned above, it is already known that the carbon can catalyze the esterification between acetic acid and ethanol. However, it is now found for the first time that the carbon can also catalyze both the esterification between ethanol and a higher fatty acid and the transesterification between ethanol and a higher fatty acid triglyceride.

It is known that the types of a catalyst used for the esterification between ethanol and acetic acid and a catalyst used for the esterification between ethanol and a higher fatty acid are different from each other. For example, hydrated niobic acid ($Nb_2O_5 \cdot nH_2O$), Nafion or the like can be used as a catalyst for the former esterification, but cannot be usually used as a catalyst for the latter esterification. Therefore, it is quite unpredictable at the time of filing the present application that the above-mentioned carbon can catalyze the esterification between ethanol and a higher fatty acid.

Based on the findings mentioned above, the present invention has been accomplished.

That is, the present invention provides the following items (1) to (12).

(1) A process for producing a higher fatty acid ester, comprising reacting a lower alcohol with a higher fatty acid in the presence of an amorphous carbon having a sulfonate group introduced therein, thereby producing the higher fatty acid ester.

(2) The process for producing a higher fatty acid ester according to Item (1), wherein the higher fatty acid is a fatty acid having 5 or more carbon atoms.

(3) The process for producing a higher fatty acid ester according to Item (1) or (2), wherein the lower alcohol is ethanol or methanol.

(4) The process for producing a higher fatty acid ester according to any one of Items (1) to (3), wherein the amorphous carbon having a sulfonate group introduced therein has a sulfonate density of 1 mmol/g or more and an integral intensity ratio of D band to G band in Raman spectra of 0.1 to 0.7.

(5) A process for producing a higher fatty acid ester, comprising reacting a lower alcohol with a higher fatty acid and a higher fatty acid triglyceride in the presence of an amorphous carbon having a sulfonate group introduced therein, thereby producing the higher fatty acid ester by both of the reaction between the lower alcohol and the higher fatty acid and the reaction between the lower alcohol and the higher fatty acid triglyceride.

(6) The process for producing a higher fatty acid ester according to Item (5), wherein the higher fatty acid is a fatty acid having 5 or more carbon atoms.

(7) The process for producing a higher fatty acid ester according to Item 5 or 6, wherein the lower alcohol is ethanol or methanol.

(8) The process for producing a higher fatty acid ester according to any one of Items (5) to (7), wherein the amorphous carbon having a sulfonate group introduced therein has a sulfonate density of 1 mmol/g or more and an integral intensity ratio of D band to G band in Raman spectra of 0.1 to 0.7.

(9) A process for producing a higher fatty acid ester, comprising: reacting a lower alcohol with a higher fatty acid and a higher fatty acid triglyceride in the presence of an amorphous carbon having a sulfonate group introduced therein, thereby producing the higher fatty acid ester by both of the reaction between the lower alcohol and the higher fatty acid and the reaction between the lower alcohol and the higher fatty acid triglyceride; and reacting the unreacted lower alcohol with the unreacted higher fatty acid triglyceride in the presence of an alkali hydroxide, thereby producing the higher fatty acid ester.

(10) The process for producing a higher fatty acid ester according to Item (9), wherein the higher fatty acid is a fatty acid having 5 or more carbon atoms.

(11) The process for producing a higher fatty acid ester according to Item (9) or (10), wherein the lower alcohol is ethanol or methanol.

(12) The process for producing a higher fatty acid ester according to any one of Items (9) to (11), wherein the amorphous carbon having a sulfonate group introduced therein has a sulfonate density of 1 mmol/g or more and an integral intensity ratio of D band to G band in Raman spectra of 0.1 to 0.7.

Effect of the Invention

As mentioned above, in the esterification using a liquid acid catalyst, an enormous amount of energy is required for the separation of the acid. In the method according to the present invention, however, a product can be separated from a catalyst readily because a solid acid catalyst is used.

Further, in the method according to the present invention, a higher fatty acid ester can be produced from a feed oil in one step. After the reaction is completed, although a layer of a higher fatty acid ester, a layer of a mixture of glycerin and water, and a solid catalyst appear in a reaction vessel, these three components can be separated from one another readily.

BEST MODE FOR CARRYING OUT THE INVENTION

Figure 1:
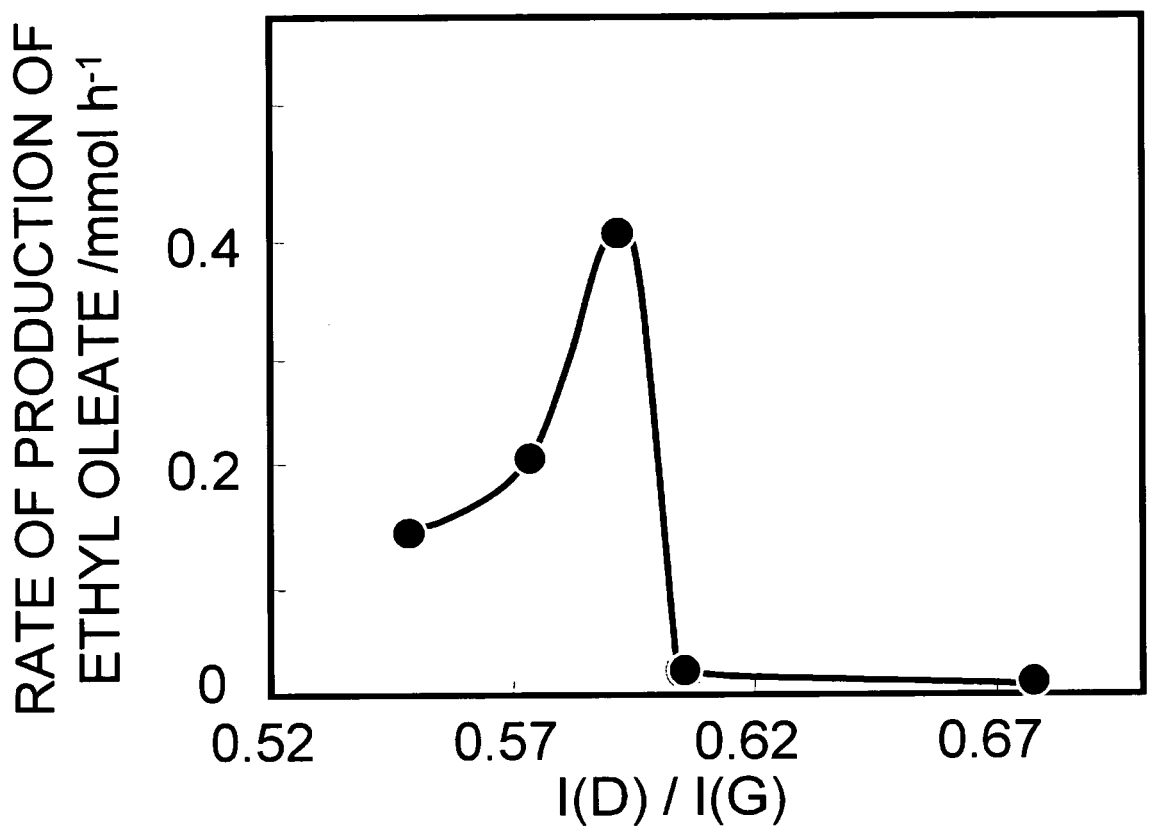
FIG. 1 is an illustration showing the relationship between the integral intensity ratio of D band to G band in Raman spectra of an amorphous carbon having a sulfonate group introduced therein and the rate of production of ethyl oleate.

Hereinbelow, the present invention will be described in detail.

Firstly, an amorphous carbon having a sulfonate group introduced therein to be used in the method for producing a higher fatty acid ester of the present invention will be described.

The term "an amorphous carbon having a sulfonate group introduced therein (also referred to as "a sulfonate-group-introduced amorphous carbon")" as used herein means a carbon which has a sulfonate group and does not have a precise crystalline structure, unlike diamond or graphite.

The sulfonate-group-introduced amorphous carbon to be used is not particularly limited, as long as it can catalyze the esterification between a lower alcohol and a higher fatty acid or the transesterification between a lower alcohol and a higher fatty acid triglyceride. For example, a sulfonate-group-introduced amorphous carbon as disclosed in International Publication No. WO 2005/029508 or a solid acid as disclosed in Japanese Patent Publication Laid-open No. 2004-238311 can be used as the sulfonate-group-introduced amorphous carbon.

An preferred example of the sulfonate-group-introduced amorphous carbon is a carbon which has both G band and D band detected in spectra obtained by Raman spectroscopy, wherein an integral intensity ratio of the D band to the G band [I(D)/I(G)] ranges from 0.1 to 0.7. If the integral intensity ratio is less than 0.3, the number of gathered 6-membered carbon rings is small and the carbon does not take a solid form. If the integral intensity ratio exceeds 0.7, on the other hand, the graphene sheet becomes large and the sulfonate density is reduced, and therefore the carbon cannot act as a catalyst. It is preferred that the integral intensity ratio be 0.1 to 0.7, preferably 0.1 to 0.65, more preferably 0.1 to 0.6. The terms "D band", "G band" and the "integral intensity ratio of D band to G band" as used herein are defined as follows.

D band is derived from an A1g breathing mode vibration in a 6-membered carbon ring, and its peak top appears at 1350 to 1360 $cm^{-1}$.

G band is derived from an E2g mode vibration in a 6-membered carbon ring, and its peak top appears at 1580 $cm^{-1}\pm 5$ $cm^{-1}$.

Raman spectra formed from the sum of these peaks is peak-split by Gaussian or Gaussian-Lorentzian. The obtained integral intensity values for D band and G band are employed as the integral intensities for these bands.

It is preferred that the sulfonate-group-introduced amorphous carbon have a sulfonate density of 1.0 mmol/g or more, preferably 1.6 mmol/g or more, more preferably 3 mmol/g or more. The upper limit of the sulfonate density is not particularly limited, and the sulfonate density is preferably not more than 8 mmol/g.

The sulfonate-group-introduced amorphous carbon can be produced by conducting a heating treatment of an organic compound in concentrated sulfuric acid or fuming sulfuric acid, as disclosed in International Publication No. WO 2005/029508 pamphlet.

In order to produce an amorphous carbon having a higher sulfonate density, it is required that the heating treatment of an organic compound in concentrated sulfuric acid or fuming sulfuric acid be conducted in a stream of an inert gas (e.g., a nitrogen, argon gas) or dry air. More preferably, the treatment is conducted by heating the concentrated sulfuric acid or fuming sulfuric acid containing the organic compound while blowing an inert gas (e.g., a nitrogen or argon gas) or dry air thereinto. The reaction of concentrated sulfuric acid with an aromatic compound can produce an aromatic sulfonic acid and water. This reaction is an equilibrium reaction. Therefore, if the amount of water is increased in the reaction system, then the reaction proceeds rapidly in a reverse direction, resulting in the remarkable decrease in the number of sulfonate groups introduced into an amorphous carbon. Accordingly, an amorphous carbon having a higher sulfonate density can be synthesized by conducting the reaction in a stream of an inert gas or dry air or while blowing such a gas into the reaction system, and then removing water from the reaction system eagerly.

In the heating treatment, the partial carbonization, cyclization, condensation or the like of the organic compound is allowed to proceed, and the sulfonation of the organic compound is allowed to occur. The temperature for the heating treatment is not particularly limited, as long as these reactions proceed at that temperature. From an industrial viewpoint, it is preferred that the temperature be 100 to 350° C., preferably 150 to 250° C. If the temperature for the heating treatment is below 100° C., then the condensation or carbonization of the organic compound proceeds unsatisfactorily and, consequently, the carbon might be formed insufficiently. If the temperature for the heating treatment exceeds 350° C., then a sulfonate group might be thermally decomposed.

The time for the heating treatment can be selected properly depending on the type of the organic compound used and the temperature employed for the heating treatment. In general, the heating treatment is conducted for 5 to 50 hours, preferably for 10 to 20 hours.

The amount of concentrated sulfuric acid or fuming sulfuric acid used is not particularly limited. In general, concentrated sulfuric acid or fuming sulfuric acid is used in an amount of 2.6 to 50.0 mol, preferably 6.0 to 36.0 mol, per 1 mol of the organic compound.

As for the organic compound, an aromatic hydrocarbon may be used. Other organic compound such as a natural substance (e.g., glucose, sugar (sucrose), cellulose) and a synthetic polymeric compound (e.g., polyethylene, polyacrylamide) may also be used. The aromatic hydrocarbon may be a polycyclic or monocyclic aromatic hydrocarbon. Specific examples include benzene, naphthalene, anthracene, perylene and coronene, and naphthalene or the like is preferably used. The organic compound may be used singly, or two or more types of organic compounds may be used in combination. The organic compound is not necessarily in a purified form. For example, heavy oil, pitch, tar, asphalt or the like which contains an aromatic hydrocarbon may be used.

When a natural substance such as glucose and cellulose or a synthetic polymeric compound is used as a starting material, it is preferred that the starting material be heated in an inert gas stream to cause the partial carbonization of the starting material prior to the heating treatment in concentrated sulfuric acid or fuming sulfuric acid. In this case, the temperature for the heating treatment is generally 100 to 350° C., and the time for the treatment is generally 1 to 20 hours.

When an aromatic hydrocarbon or heavy oil, pitch, tar, asphalt or the like which contains an aromatic hydrocarbon is used as a starting material, it is preferred that, after the heating treatment in concentrated sulfuric acid or fuming sulfuric acid, a product yielded by the heating treatment be heated in vacuo. This step enables to remove excess sulfuric acid, accelerate the carbonization or solidification of the product and increase the yield of the product. The vacuum evacuation is preferably conducted by using a vacuum evacuation apparatus having an outgassing rate of 10 L/min or more and an ultimate pressure of 100 torr or lower. The temperature for the heating is preferably 140 to 300° C., more preferably 200 to 280° C. The time for the vacuum evacuation at this temperature is generally 2 to 20 hours.

The sulfonate-group-introduced amorphous carbon can catalyze the esterification between a lower alcohol and a higher fatty acid. Thus, as a first embodiment of the process for producing a higher fatty acid ester according to the present invention, a process is provided which is characterized by reacting a lower alcohol with a higher fatty acid in the presence of an amorphous carbon having a sulfonate group introduced therein to produce the higher fatty acid ester.

In the first embodiment of the process, the lower alcohol used may be ethanol, methanol or the like, and is particularly preferably ethanol.

The higher fatty acid used is not particularly limited, and a fatty acid which can produce a fatty acid ester usable as a biodiesel oil is preferably used. Examples of the fatty acid include oleic acid, stearic acid, linoleic acid, palmitic acid and linolenic acid. The number of carbon atoms contained in the higher fatty acid is not particularly limited, and is preferably 5 or more.

The amounts of the lower alcohol and the higher fatty acid used are not particularly limited. The higher fatty acid is preferably used in an amount of 0.01 to 0.5 mol, more preferably 0.05 to 0.3 mol, per 1 mol of the lower alcohol. The amount of the sulfonate-group-introduced amorphous carbon used is not also particularly limited, and is preferably 0.1 to 20 g, more preferably 0.5 to 10 g, per 1 mol of the lower alcohol.

The temperature during the reaction is not particularly limited, and is preferably 60 to 180° C., more preferably 80 to 120° C.

The sulfonate-group-introduced amorphous carbon can also catalyze the transesterification between a lower alcohol and a higher fatty acid triglyceride. Thus, as a second embodiment of the process for producing a higher fatty acid ester according to the present invention, a process is provided which is characterized by reacting a lower alcohol with a higher fatty acid and a higher fatty acid triglyceride in the presence of an amorphous carbon having a sulfonate group introduced therein to produce the higher fatty acid ester by both of the reaction between the lower alcohol and the higher fatty acid and the reaction between the lower alcohol and the higher fatty acid triglyceride.

The higher fatty acid and the lower alcohol used may be the same as those used in the first embodiment of the process. As for the higher fatty acid triglyceride, a triglyceride containing the above-mentioned higher fatty acid may be used.

The amounts of the lower alcohol, the higher fatty acid and the higher fatty acid triglyceride used are not particularly limited. It is preferred that the higher fatty acid be used in an amount of 0.01 to 0.5 mol, more preferably 0.05 to 0.3 mol, and the higher fatty acid triglyceride be used in an amount of 0.01 to 0.5 mol, more preferably 0.05 to 0.3 mol, per 1 mol of the lower alcohol. The amount of the sulfonate-group-introduced amorphous carbon used is not also particularly limited, and is preferably 0.1 to 20 g, more preferably 0.5 to 10 g, per 1 mol of the lower alcohol.

The temperature during the reaction is not particularly limited, and is preferably 60 to 180° C., more preferably 80 to 120° C.

In the second embodiment of the process, such a case may occur that the free higher fatty acid is consumed completely and only the higher fatty acid triglyceride remains unreacted. In this case, for the purpose of further producing a higher fatty acid ester from the unreacted higher fatty acid triglyceride, as a third embodiment of the process for producing a higher fatty acid ester according to the present invention, a process is provided which is characterized by: reacting a lower alcohol with a higher fatty acid and a higher fatty acid triglyceride in the presence of an amorphous carbon having a sulfonate group introduced therein, thereby producing the higher fatty acid ester by both of the reaction between the lower alcohol and the higher fatty acid and the reaction between the lower alcohol and the higher fatty acid triglyceride; and then reacting the unreacted lower alcohol with the unreacted higher fatty acid triglyceride in the presence of an alkali hydroxide, thereby producing the higher fatty acid ester.

The reaction in the first stage of the third embodiment of the process can be conduced in the same manner as the second embodiment of the process.

The alkali hydroxide used in the reaction in the latter stage of the third embodiment of the process may be one which is generally used as a transesterification catalyst, such as sodium hydroxide, an anion exchange resin having a basic functional group (e.g., an amine) bound thereto, magnesium oxide and calcium oxide.

The temperature for the reaction in the latter stage of the third embodiment of the process is not particularly limited, and is preferably 60 to 180° C., more preferably 80 to 120° C.

The process for producing a higher fatty acid ester according to the present invention enables to produce a higher fatty acid ester by using any one of various types of oils as a starting material. Examples of the oil to be used as the starting material include soy bean oil, sunflower oil, palm oil, coconut oil, microalgae oil and wood oil. In addition, a waste oil discharged from a home or factory or the like can also be used as the starting material.

EXAMPLES

Hereinafter, the present invention will be described in great detail with reference to the following examples.

Example 1

Twenty grams (20 g) of D-glucose was heated at 400° C. for 15 hours under a nitrogen gas stream to produce a carbonaceous powder. The powder was heated at 150° C. for 15 hours while stirring in 200 ml of 15-wt % fuming sulfuric acid to produce a black powder. The black powder was washed with distilled water repeatedly to remove sulfuric acid contained in the black powder, thereby producing a sulfonate-group-introduced amorphous carbon.

The sulfonate-group-introduced amorphous carbon had a sulfonate density of 1.5 mmol/g and an integral intensity ratio of D band to G band [I(D)/I(G)] in Raman spectra of 0.59.

The determination of a sulfonate density was made in the following manner. Since almost all of element sulfur contained in the sulfonate-group-introduced amorphous carbon was derived from a sulfonate group, the amount of sulfur contained in a sample was quantified by elemental analysis by burning (SX-Elements Micro Analyzer YS-10 (yanaco)) to determine the amount of a sulfonate.

The integral intensity ratio of D band to G band in Raman spectra was determined in the following manner. A sample powder was placed in a sample holder in NRS-2100 type triple monochrometer Raman spectrometer (JASCO Corporation) and Raman spectra were measured. The Raman spectra in which both D band and G band were observed were subjected to peak split into two peaks, i.e., D band and G band, using Gaussian or Gaussian-Lorentzian, and the obtained integral intensity values for D band and G band were employed as the integral intensities of these bands.

A mixture of ethanol and oleic acid (ethanol: 0.1 mol, oleic acid: 0.01 mol) was added with 0.2 g of the sulfonate-group-introduced amorphous carbon, and the resulting mixture was maintained at 80° C. to produce ethyl oleate. The amount of ethyl oleate produced was quantified on a gas chromatography-mass spectrometer (Shimadzu GCMS-QP5050). The rate of production of ethyl oleate was 0.42 mmol/h, which was 10 times or more greater than that achieved using the same weight of a polymeric solid acid "Nafion" (an already-existing solid acid having a high acid catalyst activity) as a catalyst and exceeds 50% of that achieved using the same weight of sulfuric acid as a catalyst.

Example 2

A mixture of ethanol and oleic acid triglyceride (ethanol: 0.1 mol, oleic acid triglyceride: 0.01 mol) was added with 0.2 g of the sulfonate-group-introduced amorphous carbon synthesized in Example 1, and the resulting mixture was maintained at 80° C. for 12 hours to produce ethyl oleate. The amount of ethyl oleate produced was quantified on a gas chromatography-mass spectrometer. The yield of ethyl oleate was 30%, and the rate of production of ethyl oleate was 10 to 100 times greater than that achieved using the same weight of each of already-existing solid strong acids (hydrated niobic acid, a polymeric solid acid "Nafion", and a polymeric solid acid "Amberlyst-15") as a catalyst.

Comparative Example 1

A sulfonate-group-introduced amorphous carbon was produced in the same manner as that in Example 1, except that the temperature for heating D-glucose was 550° C.

The sulfonate density and the I(D)/I(G) ratio in Raman spectra of the sulfonate-group-introduced amorphous carbon were determined in the same manner as in Example 1, and it was found that the sulfonate-group-introduced amorphous carbon had a sulfonate density of 0.1 mmol/g and an I(D)/I(G) ratio of 0.75.

A mixture of ethanol and oleic acid (ethanol: 0.1 mol, oleic acid: 0.01 mol) was added with 0.2 g of the sulfonate-group-introduced amorphous carbon, and the resulting mixture was maintained at 80° C. It was tried to quantify the amount of ethyl oleate produced on a gas chromatography-mass spectrometer. However, no production of ethyl oleate was observed.

Comparative Example 2

A mixture of ethanol and oleic acid triglyceride (ethanol: 0.1 mol, oleic acid triglyceride: 0.01 mol) was added with 0.2 g of the sulfonate-group-introduced amorphous carbon synthesized in Comparative Example 1, and the resulting mixture was maintained at 80° C. for 12 hours. It was tried to quantify the amount of ethyl oleate produced on a gas chromatography-mass spectrometer. However, no production of ethyl oleate was confirmed.

Test Example

Besides the sulfonate-group-introduced amorphous carbon synthesized in Example 1 (I(D)/I(G)=0.59), other four types of sulfonate-group-introduced amorphous carbons having different I(D)/I(G) ratios were synthesized. These amorphous carbons were used in the same manner as in Example 1 to produce ethyl oleate, and the rates of production of ethyl oleate were determined (FIG. 1).

What is claimed is:

1. A process for producing a higher fatty acid ester, which comprises
   reacting a lower alcohol with a higher fatty acid in the presence of an amorphous carbon having a sulfonate group introduced therein, thereby producing the higher fatty acid ester,
   wherein the amorphous carbon having a sulfonate group introduced thereon is produced by sulfonation of an amorphous carbon at a temperature of 100 to 350° C. for 5 to 50 hours and the amorphous carbon having a sulfonate group has an integral intensity ratio of D band to G band in Raman spectra of 0.1 to 0.7.

2. The process for producing a higher fatty acid ester according to claim 1, wherein the higher fatty acid is a fatty acid having 5 or more carbon atoms.

3. The process for producing a higher fatty acid ester according to claim 1 or 2, wherein the lower alcohol is ethanol or methanol.

4. The process for producing a higher fatty acid ester according to claim 1, wherein the amorphous carbon having a sulfonate group introduced therein has a sulfonate density of 1 mmol/g or more and an integral intensity ratio of D band to G band in Raman spectra of 0.1 to 0.65.

5. A process for producing a higher fatty acid ester, which comprises
   reacting a lower alcohol with a higher fatty acid and a higher fatty acid triglyceride in the presence of an amorphous carbon having a sulfonate group introduced therein, thereby producing the higher fatty acid ester by both of the reaction between the lower alcohol and the higher fatty acid and the reaction between the lower alcohol and the higher fatty acid triglyceride,
   wherein the amorphous carbon having a sulfonate group introduced thereon is produced by sulfonation of an amorphous carbon at a temperature of 100 to 350° C. for 5 to 50 hours and the amorphous carbon having a sulfonate group has an integral intensity ratio of D band to G band in Raman spectra of 0.1 to 0.7.

6. The process for producing a higher fatty acid ester according to claim 5, wherein the higher fatty acid is a fatty acid having 5 or more carbon atoms.

7. The process for producing a higher fatty acid ester according to claim 5 or 6, wherein the lower alcohol is ethanol or methanol.

8. The process for producing a higher fatty acid ester according to claim 5, wherein the amorphous carbon having a sulfonate group introduced therein has a sulfonate density of 1 mmol/g or more and an integral intensity ratio of D band to G band in Raman spectra of 0.1 to 0.65.

9. A process for producing a higher fatty acid ester, which comprises
   reacting a lower alcohol with a higher fatty acid and a higher fatty acid triglyceride in the presence of an amorphous carbon having a sulfonate group introduced therein, thereby producing the higher fatty acid ester by both of the reaction between the lower alcohol and the higher fatty acid and the reaction between the lower alcohol and the higher fatty acid triglyceride; and
   reacting the unreacted lower alcohol with the unreacted higher fatty acid triglyceride in the presence of an alkali hydroxide, thereby producing the higher fatty acid ester,
   wherein the amorphous carbon having a sulfonate group introduced thereon is produced by sulfonation of an amorphous carbon at a temperature of 100 to 350° C. for 5 to 50 hours and an integral intensity ratio of D band to G band in Raman spectra of 0.1 to 0.7.

10. The process for producing a higher fatty acid ester according to claim 9, wherein the higher fatty acid is a fatty acid having 5 or more carbon atoms.

11. The process for producing a higher fatty acid ester according to claim 9 or 10, wherein the lower alcohol is ethanol or methanol.

12. The process for producing a higher fatty acid ester according to claim 9, wherein the amorphous carbon having a sulfonate group introduced therein has a sulfonate density of 1 mmol/g or more and an integral intensity ratio of D band to G band in Raman spectra of 0.1 to 0.65.

13. The method of claim 1, wherein the temperature is between 150 to 250° C.

14. The method of claim 5, wherein the temperature is between 150 to 250° C.

15. The method of claim 9, wherein the temperature is between 150 to 250° C.

16. The method of claim 1, wherein the sulfonation is for 10 to 20 hours.

* * * * *